US009848966B2

(12) United States Patent
Chodorow et al.

(10) Patent No.: US 9,848,966 B2
(45) Date of Patent: Dec. 26, 2017

(54) HYBRID DENTAL DEVICE

(71) Applicant: Sacks Holdings, Inc., Solana Beach, CA (US)

(72) Inventors: Devin S. Chodorow, Rancho Santa Fe, CA (US); Ingram S. Chodorow, Rancho Santa Fe, CA (US)

(73) Assignee: SACKS HOLDINGS, INC., Solana Beach, CA (US)

( * ) Notice: Subject to any disclaimer, the term of this patent is extended or adjusted under 35 U.S.C. 154(b) by 0 days.

(21) Appl. No.: 14/546,961

(22) Filed: Nov. 18, 2014

(65) Prior Publication Data

US 2015/0305840 A1 Oct. 29, 2015

Related U.S. Application Data

(60) Provisional application No. 61/985,989, filed on Apr. 29, 2014.

(51) Int. Cl.
*A61C 15/00* (2006.01)
*A61C 15/02* (2006.01)
*A61C 15/04* (2006.01)

(52) U.S. Cl.
CPC ............ *A61C 15/02* (2013.01); *A61C 15/046* (2013.01)

(58) Field of Classification Search
CPC .......... A61C 15/00; A61C 15/02; A61C 15/04
USPC ..................................................... D28/65–68
See application file for complete search history.

(56) References Cited

U.S. PATENT DOCUMENTS

| | | | | | |
|---|---|---|---|---|---|
| 2,877,547 | A | * | 3/1959 | Feaster | ............................ 30/1 |
| 4,332,409 | A | * | 6/1982 | Stachowicz | ..................... 294/2 |
| D637,762 | S | * | 5/2011 | Nanda | ........................... D28/65 |
| 2011/0132392 | A1 | * | 6/2011 | Crisp | ................ A46B 15/0055 |
| | | | | | 132/309 |
| 2012/0103356 | A1 | * | 5/2012 | Crisp | ........................... 132/200 |
| 2012/0111348 | A1 | * | 5/2012 | Prokopchuk et al. | ........ 132/200 |
| 2014/0007899 | A1 | * | 1/2014 | Berry et al. | .................. 132/309 |

* cited by examiner

*Primary Examiner* — Rachel Steitz
(74) *Attorney, Agent, or Firm* — Kilpatrick Townsend & Stockton LLP

(57) ABSTRACT

A hybrid dental tool is disclosed herein. The hybrid dental tool includes a flossing head and a handle portion. The flossing head can include a filament stretching between the leading arm and a trailing arm. The flossing head can be connected to the handle portion. The handle portion can include features that can receive and retain a pick. The pick can be a soft pick or a hard pick. The handle portion can further include an integrated pick that can be located at a free end of the handle portion.

9 Claims, 6 Drawing Sheets

HYBRID DENTAL DEVICE

CROSS-REFERENCES TO RELATED APPLICATIONS

This application claims the benefit of U.S. Provisional Application No. 61/985,989 entitled "HYBRID DENTAL DEVICE," and filed on Apr. 29, 2014, the entirety of which is hereby incorporated by reference herein.

BACKGROUND

The present invention relates, generally, to dental devices, and more particularly to dental hygiene devices.

While dental hygiene has long been important in American and other cultures for maintaining a desirable physical appearance, recent discoveries have increased the urgency with which dental hygiene is maintained. These recent discoveries have linked oral bacteria to other, more serious diseases such as, for example, heart disease. In light of the increased importance of dental hygiene, new devices are desired to improve dental hygiene.

BRIEF SUMMARY

One aspect of the present disclosure relates to a hybrid dental device. The hybrid dental device includes a pick including a shaft and a cleaner, and a flosser. In some embodiments, the flosser includes a flossing portion and a handle, which handle can include a pick depression. In some embodiments, the pick depression can receive the shaft and the cleaner of the pick. The handle can include a pick retainer. In some embodiments, the pick retainer can retain the pick within the pick depression.

In some embodiments, the flossing portion includes a leading arm and a trailing arm that can be, for example, connected by a link arm. In some embodiments, a filament extends from the leading arm to the trailing arm, which filament can be, for example, dental floss. In some embodiments, the link arm can include a bite plate that can extend parallel to the filament. In some embodiments, the pick retainer can include a channel that can receive a portion of the pick.

In some embodiments of the hybrid dental device, the channel can include a first dimension. In some embodiments, the first dimension can be smaller than a width of the cleaner. In some embodiments, the width of the cleaner can be measured perpendicular to the shaft of the pick and/or can be measured at the widest portion of the pick. In some embodiments, the cleaner of the pick can be deformable to allow movement of the cleaner through the channel.

In some embodiments, the pick retainer can include at least one feature that can deformably engage with the pick. In some embodiments, the handle can include a connecting end and a free end. In some embodiments, the connecting end of the handle connects the handle to the flosser. In some embodiments, the hybrid dental device further includes a second pick located at the free end of the handle. In some embodiments, the second pick can be a soft pick or a hard pick.

One aspect of the present disclosure relates to a hybrid dental device. The hybrid dental device includes a pick having a shaft and a cleaner and a flosser. In some embodiments, the flosser includes a flossing portion, and a handle having a pick retainer that can detachably connect the pick to the handle.

In some embodiments of the hybrid dental device, the flossing portion can have a leading arm and a trailing arm connected by a link arm. In some embodiments, the link arm can have a bite plate extending parallel to the filament. In some embodiments, the pick can be a soft pick. In some embodiments, the handle can have a connecting end and a free end, which connecting end of the handle connects the handle to the flosser, and which the free end is distal from the connection of the connecting end and the flosser. In some embodiments, the hybrid dental device can include a second pick located at the free end of the handle, which second pick is protected by the pick when the pick is detachably connected to the handle.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION

In some embodiments, the present disclosure relates to a hybrid dental device and/or hybrid dental tool. In some embodiments, the hybrid dental tool can integrate multiple care devices into a single device. In some embodiments, the hybrid dental tool can include a flosser and one or several picks. In some embodiments, the one or several picks can be integrated into the flosser, and/or retained by the flosser. In one embodiment, a first pick, which can be, for example, a soft pick, can be retained in a handle portion of the flosser. In some embodiments, a second pick which can be, for example, a hard pick, can be formed into a portion of the handle of the flosser.

For the purposes of explanation, the ensuing details are set forth in order to provide a thorough understanding of various embodiments. It will be apparent, however, to one skilled in the art that various embodiments may be practiced without some of these specific details. For example, various features may be shown as components of some specific embodiments. In other instances, previously known features may be shown without unnecessary detail in order to avoid obscuring the inventive features of the described embodiments.

Embodiments provided herein are examples only, and are not intended to limit the scope, applicability, or configuration of the disclosure. Rather, the ensuing description of the embodiments will provide those skilled in the art with an enabling description for implementing one or more embodiments. It should be understood that various changes may be made in the function and arrangement of elements without departing from the spirit and scope of the disclosed embodiments.

Figure 1:
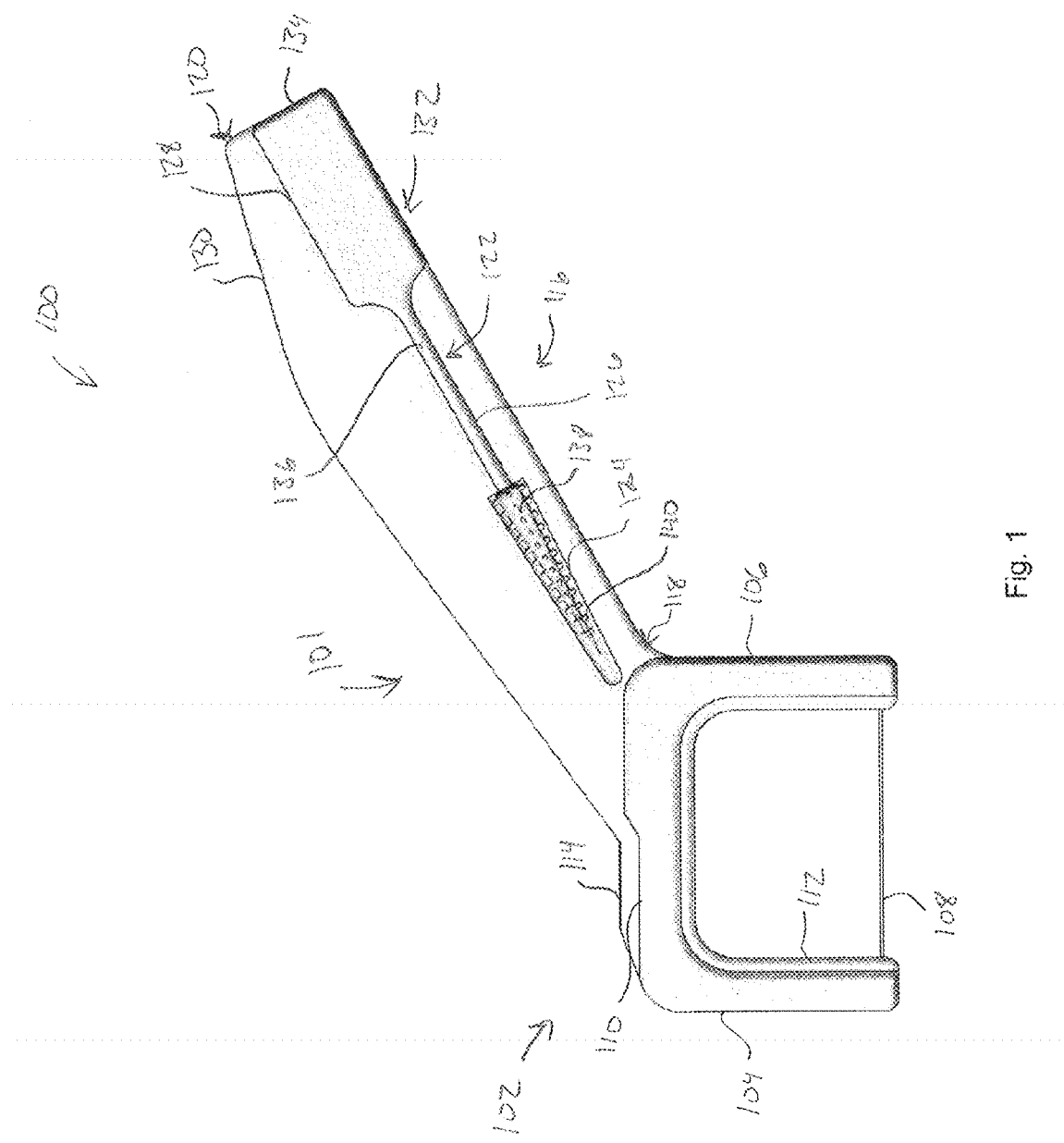
FIG. 1 is a front view of one embodiment of hybrid dental tool.

With reference now to FIG. 1, a front view of one embodiment of a hybrid dental tool 100 is shown. The hybrid dental tool 100 can comprise a variety of shapes and sizes. In some embodiments, the hybrid dental tool can be sized so as to be easily held in a hand and to be used within a mouth. The hybrid dental tool 100 can be made from a variety materials. In some embodiments, the hybrid dental tool 100 can be made from one or several plastics, metals, composites, polymers, or the like. In some embodiments, the materials for the hybrid dental tool 100 are selected based on desired properties of a hybrid dental tool and/or of the specific portion of the hybrid dental tool.

The hybrid dental tool 100 can include a flosser 101. The flosser 101 includes a flossing head 102, also referred to herein as a flossing portion or a flosser. The flossing head 102 can include features configured to allow use of the hybrid dental tool 100 and flossing teeth. The flossing head 102 can comprise a variety of shapes and sizes, but should be a size and shape so as to allow a user to access all of the teeth in the user's mouth, and particularly the teeth located in the rear of the mouth.

The flossing head 102 can include a leading arm 104 and a trailing arm 106. In some embodiments, the leading arm 104 can be located at the front of the flossing head 102 and/or of the flosser 101 and the trailing arm 106 can be relatively more centrally located in the flosser 101. In some embodiments, the leading arm 104 and the trailing arm 106 are parallel, and in some embodiments, the leading arm 104 and the trailing arm 106 are nonparallel. In some embodiments, the leading arm 104 and the trailing arm both extend from a link arm 110 and are connected by a filament 108. This connection of the leading arm 104, the trailing arm 106, and the link arm 110 can create a U-shaped flossing head 102. In some embodiments, the connection of the leading arm 104, the trailing arm 106, and link arm 110 can give other shapes to the flossing head 102 such as, for example, a C-shape, a trapezoidal shape, or the like. In some embodiments, the filament 108 can be a thin single fiber and/or group of fibers that is sized, shaped, and configured for insertion between the patient's teeth. In some embodiments, the filament 108 can comprise dental floss.

As seen in FIG. 1, some or all of the leading arm 104, the trailing arm 106 and the link arm 110 can include one or several tiers 112. In some embodiments, the one or several tiers 112 can improve the appearance of the flossing head 102 and increase the rigidity of the flossing head 102. In some embodiments, the increased rigidity of the flossing head 102 can decrease the likelihood of bending and/or deformation of one of the leading arm 104, the trailing arm 106, and the link arm 110 during flossing.

As further seen in FIG. 1, in some embodiments, the link arm 110 can include a bite plate 114. In some embodiments, the bite plate 114 can be sized, shaped, and positioned so as to allow a user to bite on the bite plate 114 to increase the force with which the filament 108 is pushed between teeth during flossing. In some embodiments, the bite plate 114 can comprise a thickness and/or width that is greater than the thickness and/or width of the link arm 110. In some embodiments, this increased thickness and/or width of the bite plate 114 can increase stability of the hybrid dental tool 100 when a user is biting on the bite plate 114. In some embodiments, the bite plate 114 can extend parallel to the filament 108.

The flosser 101 can include a handle portion 116. In some embodiments, the handle portion 116 can be sized and shaped so as to allow a user to hold the handle portion 116 to control operation of the hybrid dental device 100. The handle portion 116 can include a connecting end 118 that connects to the flossing head 102, and specifically can connect to one or more of the link arm 110 and the trailing arm 106. The handle portion 116 can further include a free end 120. In some embodiments, the free end 120 is located opposite the connecting end 118, and does not directly connect to the flossing head 102, but rather connects to the flossing head 102 via the connecting end 118. In other words, the free end 120 is located distally from the connection of the connecting end 118 of the handle portion 116 to the flossing head 102.

In some embodiments, a pick can be removably attached to the handle portion 116. In some embodiments, the pick can be integral to, but separable from the handle portion 116. In one embodiment, for example, the pick can be connected to the handle portion 116 via one or several breakable connections, which connections can be broken to separate the pick from the handle portion 116. In some embodiments, the pick can be a separate component from the handle portion 116 and can be connected to the handle portion 116 via one or several features of the handle portion 116 and/or the pick. Such an embodiment is depicted in FIG. 1, wherein the handle portion 116 includes a pick receptacle 122 extending from the free end 120 towards the connecting end 118. The pick receptacle 122 can be configured to receive and/or retain a pick. In some embodiments, the pick receptacle 122 can be sized so as to receive the pick, and specifically can have one or several dimensions larger than one or several corresponding dimensions of the pick so as to thereby allow portions of the pick to be received within the pick receptacle 122. In some embodiments, the pick receptacle 122 can be a depression in the handle portion 116 of the hybrid dental device 100.

In line with the purpose of receiving some or all of the pick, the pick receptacle 122 can comprise a variety of shapes and sizes and can be located on a variety of portions of the handle portion 116. In some embodiments, the pick receptacle 122 includes a tip receptacle 124 sized and shaped to receive the tip of the pick, a shaft receptacle 126 sized and shaped to receive a shaft of the pick, and a grip receptacle 128 sized and shaped to receive some or all of the grip of the pick. In some embodiments, the tip receptacle 124, the shaft receptacle 126, and the grip receptacle 128 can receive the some or all of the pick. Thus, in some embodiments, the pick can be completely received within the volume defined by the pick receptacle 122, and in some embodiments, the pick can be partially received within the volume defined by the pick receptacle 122 and can, therefore, partially extend from the volume defined by the pick receptacle 122.

As further seen in FIG. 1, the handle portion 116 can include an extending arm 130. In some embodiments, the extending arm 130 can extend around portions of the pick receptacle 122 such as, for example, around portions of the grip receptacle 128. In some embodiments, the extending arm 130 can be configured to protect the pick from being snagged and/or to increase the ergonomics of the handle portion 116. In some embodiments, which will be discussed at greater length below, the extending arm 130 can be configured for other dental use.

The hybrid dental tool 100 can include a pick. In some embodiments, the pick can be configured for insertion between teeth to clean between the teeth. In some embodiments, the pick 132 can comprise a hard pick made of a hard material, and in some embodiments, the pick 132 can comprise a soft pick. In some embodiments, a soft pick can include a hard component which can be partially or completely covered with a soft outer layer.

The pick 132 can include a grip 134 that can be sized and shaped for manipulation by user, a shaft 136, and a tip 138 connected to the grip by the shaft 136. In some embodiments, the tip 138 can be sized and shaped to facilitate cleaning between teeth and/or to facilitate insertion between teeth. In some embodiments, for example, the tip 138 can taper to a point and can, for example, be cone shaped. In some embodiments, the tip 138 can extend to a point which can be, for example, a rounded point, and/or a sharpened point.

In some embodiments, the tip 138 can be defined by one or several of a length, a width, and a diameter. Similarly, in some embodiments, the shaft 136 can be defined by one or several of a length, a width, and a diameter. In some embodiments, the length of both the tip 138 and the shaft 136 can be measured in the direction of the extension of the shaft 136 and the tip 138 from the grip 134. In some embodiments, the width and/or diameter of the widest portion of the tip 138 can be larger than the width and/or diameter of the widest portion of the shaft 136.

The tip 138 of the pick 132 can include one or several cleaning protrusions 140. In some embodiments, the one or several cleaning protrusions 140 can be configured to massage the gums of the user and/or to improve cleaning of the area between the teeth. The cleaning protrusions 140 can comprise a variety of shapes and sizes. In some embodiments, the shapes and sizes of the cleaning protrusions 140 can be influenced by whether the pick 132 is a soft pick or a hard pick. In one embodiment, for example, the cleaning protrusions 140 can be larger when the pick 132 is a soft pick than when the pick 132 is a hard pick. In some embodiments, the one or several cleaning protrusions 140 can include a plurality of knobs regularly spaced along and around the tip 138 of the pick 132.

Figure 2:
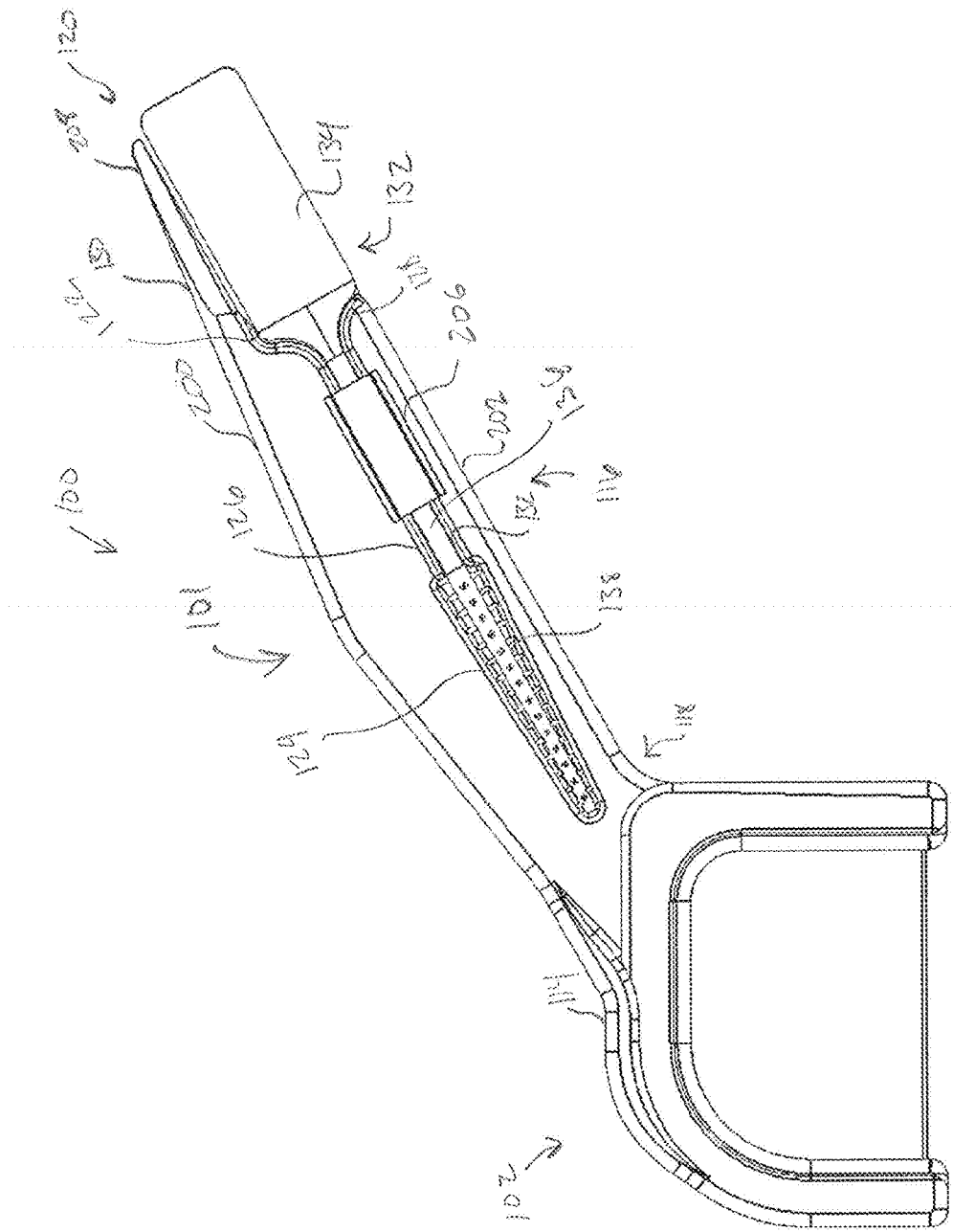
FIG. 2 is a front view of another embodiment of the hybrid dental tool.

With reference now to FIG. 2, a front view of another embodiment of the hybrid dental tool 100 is shown. As seen in FIG. 2, the hybrid dental tool 100 includes the flosser 101 having the flossing head 102 and the handle portion 116. The handle portion 116 is connected to the flossing head 102 via the connecting end 118. Opposite the connecting end 118 is the free end 120. In the embodiment depicted in FIG. 2, the pick receptacle 122 extends from the free end 120 towards the connecting end 118 of the handle portion 116. As further seen in FIG. 2, the pick 132 is retained within the pick receptacle 122, and specifically, the tip 138 of the pick 132 is located within the tip receptacle 124, the shaft 136 of the pick 132 is located within the shaft receptacle 126, and the grip 134 of the pick 132 is located, at least in part, in the grip receptacle 128. In the embodiment of the pick 132 depicted in FIG. 2, the width and/or diameter of the largest portion of the tip 138 of the pick 132 is larger than the width and/or diameter of the shaft 136 of the pick 132.

As seen in FIG. 2, the handle portion 116 includes a retention feature 206. The retention feature 206 can comprise any feature configured to retain the connection between the pick 132 and the handle portion 116. In some embodiments, the retention feature 206 can be one or several features that deformably interact with the pick 132 to retain the pick within the pick receptacle 122. In some embodiments, these features can themselves deform, can deform the pick 132, or can both deform themselves and the pick 132 to allow the retention of the pick 132 and the separation of the pick 132 from the handle portion 116. In some embodiments, these features can create a force fit and/or friction fit between the pick 132 and the pick receptacle 122. In the embodiment depicted in FIG. 2, the retention feature 206 is a covering extending over a portion of the pick receptacle 122. As seen, the covering over the portion of the pick receptacle 122 is sized to allow insertion of the tip 138 of the pick 132 into and through the volume defined by the covering and the pick receptacle 122, and to receive the shaft 136 within this volume.

The hybrid dental tool 100, and specifically the handle portion 116 of the hybrid dental tool 100 includes a handle top 200 and an opposing handle bottom 202. In the embodiment depicted in FIG. 2, the pick receptacle 122 is located relatively more proximate to the handle bottom 202 than the handle top 200. Due to this positioning of the pick receptacle 122, the extending arm 130 extends along the handle top 200 of the handle portion 116. Specifically in the embodiment depicted in FIG. 2, the extending arm 130 of the handle portion 116 is formed into an integrated pick 208. In some embodiments, the integrated pick 208 can be used for performing dental hygiene separate from the flossing head 102 and the pick 132. In some embodiments, the integrated pick 208, also referred to herein as the second pick, can be a hard pick, and in some embodiments, the integrated pick 208 can be a soft pick that can be formed by, for example, double injection molding. In such an embodiment, the hybrid dental tool 100 depicted in FIG. 2 is formed during a first step in the double injection molding process, wherein a hard plastic is injection molded to form the hybrid dental tool 100, and a second, pliable layer is applied to the integrated pick 208 during a second step of the injection molding process. Like pick 132, the integrated pick 208 can comprise a variety of shapes and sizes. In some embodiments, the integrated pick 208 can extend to a point, which point can be rounded and/or sharpened.

In some embodiments, the integrated pick 208 can be positioned such that when the pick 132 is connected to the handle portion 116 of the flosser 101, portions of the integrated pick 208, and particularly the point of the integrated pick 208, are protected by portions of the pick 132. Specifically, and as seen in FIG. 2, the grip 134 of the pick 132 is positioned adjacent to the integrated pick 208 when the pick 132 is connected to and/or retained by the handle portion 116. In such a position, the integrated pick 208 is protected by the grip 134 in that the tip of the integrated pick 208 does not extend beyond the grip 134, and thus is not easily snagged.

Figure 3:
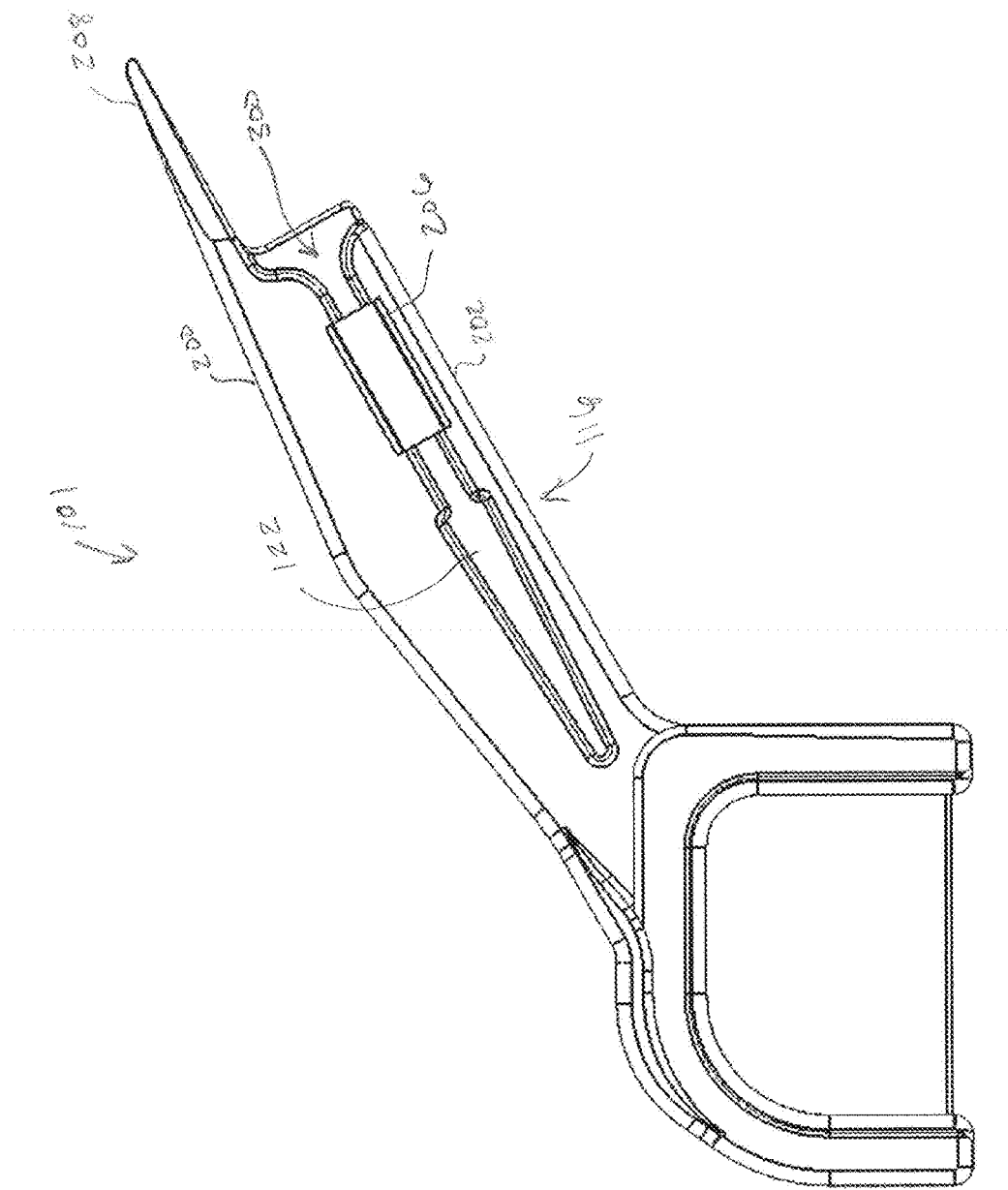
FIG. 3 is a front view of one embodiment of the flosser of the hybrid dental tool.

With reference now to FIG. 3, an embodiment of the flosser 101 is shown. As seen in FIG. 3, the flosser 101 includes a handle portion 116 having a handle top 200 and handle bottom 202. The handle portion 116 further includes a pick receptacle 122 that includes a retention feature 206 and a back plate 300. In some embodiments, the retention feature 206 defines one outer limit of the pick receptacle 122 and the back plate 300 defines an opposing outer limit of the pick receptacle 122. In the embodiment depicted in FIG. 3, the back plate 300 does not extend to the termination point of the integrated pick 208. Advantageously, this early termination of the back plate 300 allows the user to grip both sides of the grip 134 of the pick 132.

Figure 4:
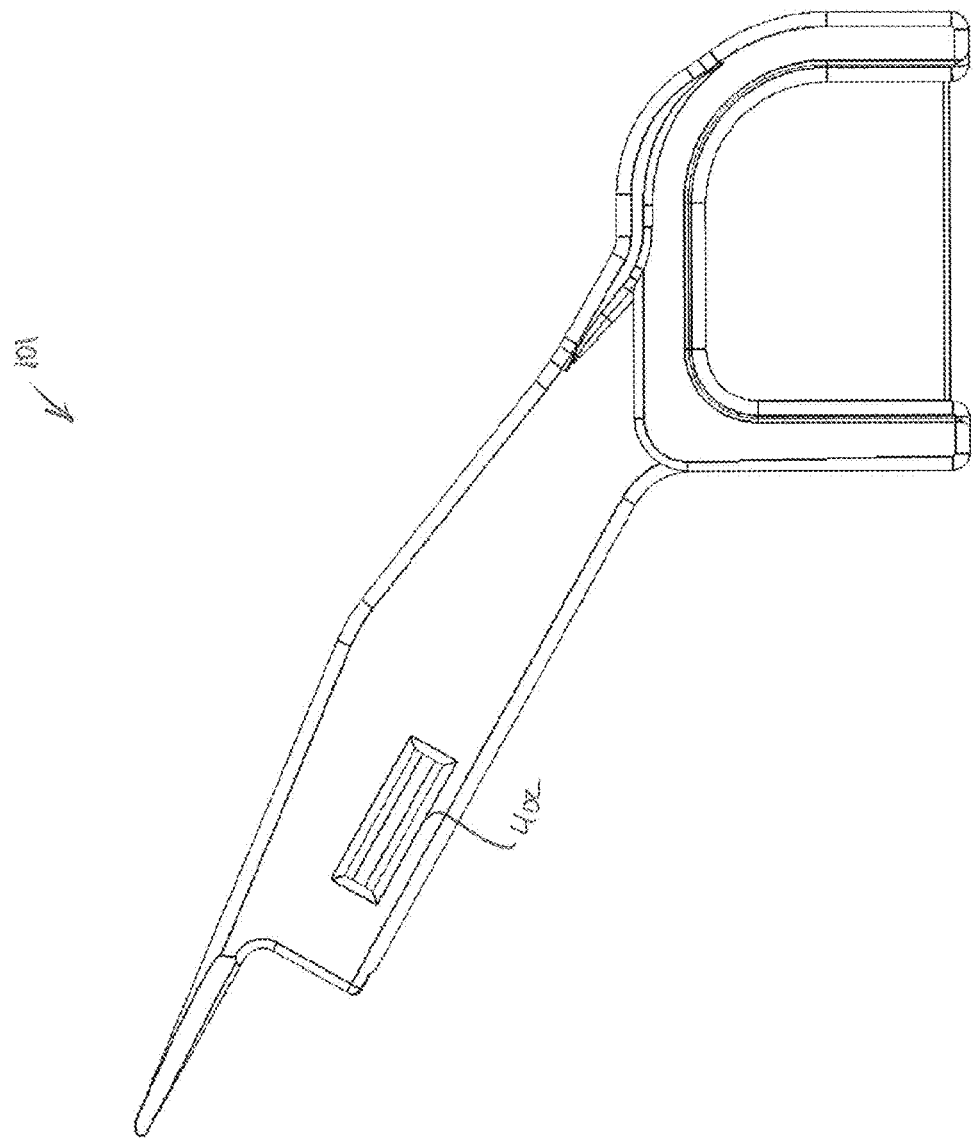
FIG. 4 is a back view of one embodiment of the flosser of the hybrid dental tool.

With reference now to FIG. 4, a back view of one embodiment of the flosser 101 is shown. As seen in FIG. 4, some embodiments of the flosser 101 can include a retention opening 402. In some embodiments, the retention opening 402 can be an opening extending up into the interior of, for example, the retention feature 206. In some embodiments, the retention opening 402 can receive a feature that can be configured to secure the pick 132 within the pick receptacle 122. In other embodiments, the retention opening 402 can merely be an artifact of an advantageous molding process.

Figure 5:
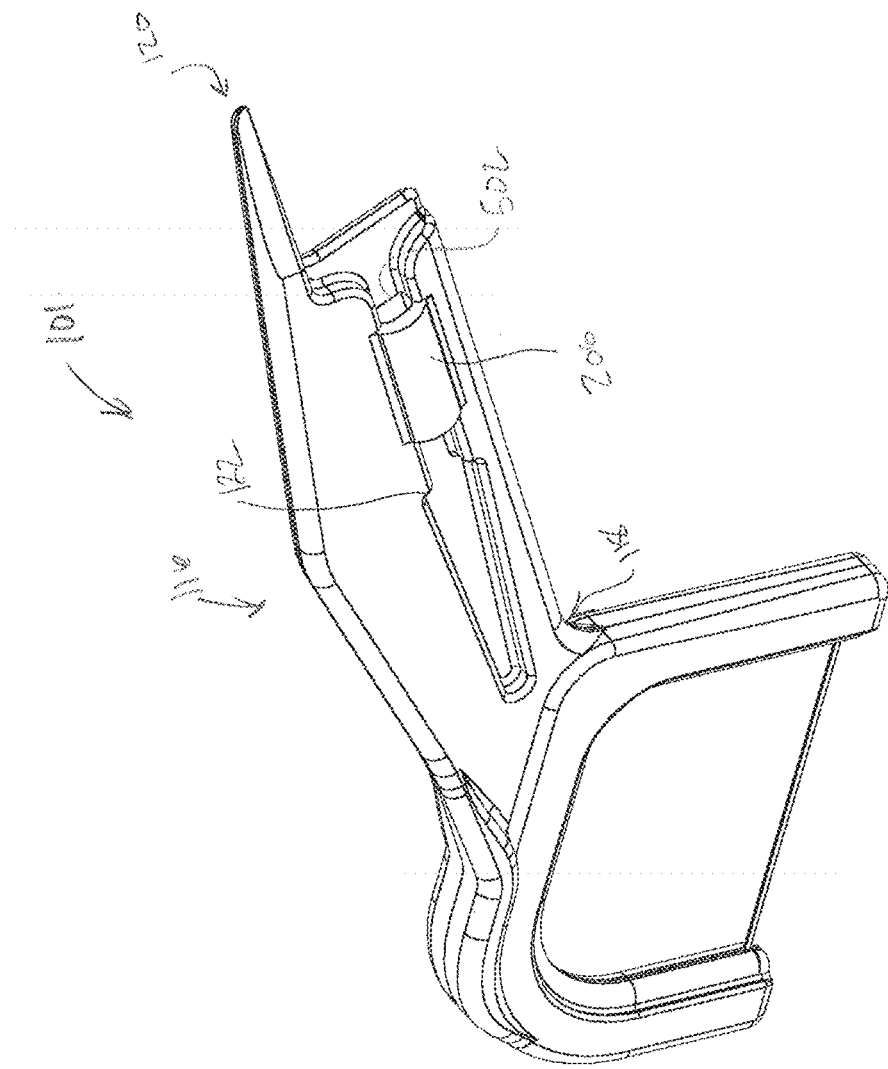
FIG. 5 is a perspective view of one embodiment of the flosser of the hybrid dental tool.

With reference now to FIG. 5, a perspective view of one embodiment of the flosser 101 is shown. As seen in FIG. 5, the retention feature 206 can comprise a channel 502, which can be, as shown in FIG. 5, for example, an enclosed channel and/or a covered channel, that can be sized and shaped to receive portions of the pick 132 and to retain the pick 132 within the pick receptacle 122. Specifically, as seen in FIG. 5, the channel 502 can have a dimension, measured perpendicular to the direction of the extension of the pick receptacle 122 in the handle portion 116 from the free end 122 the connecting end 118, that can be, for example, larger than the width and/or diameter of the shaft 136 of the pick 132. In some embodiments, the dimension of the channel 502 can be, for example, smaller than the width and/or diameter of the tip 138 of the pick. In some embodiments, this can advantageously retain the pick 132 in the pick receptacle 122 until a force is applied to the pick 132 and the handle portion 116 sufficient to deform the tip 138 of the pick 132 to allow the tip 138 to pass through the channel 502.

Figure 6:
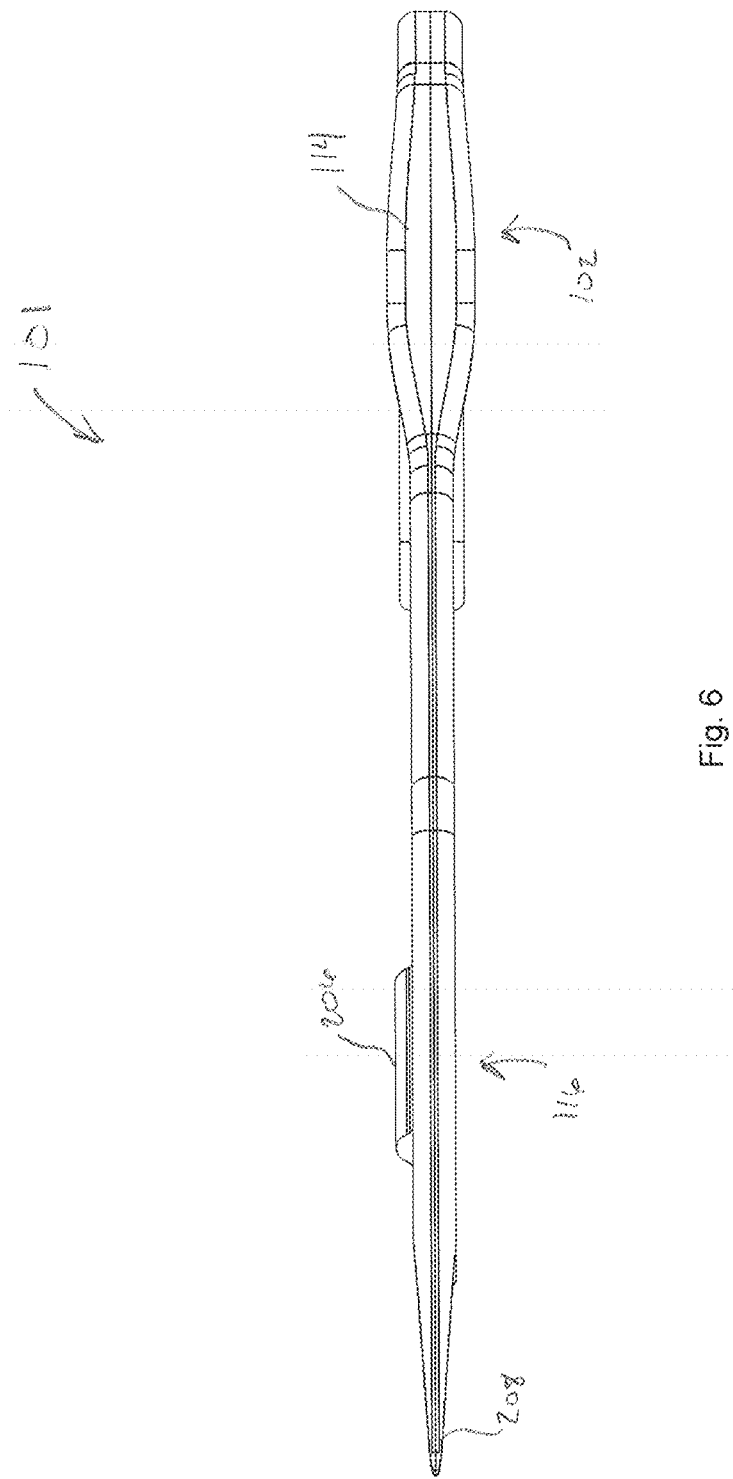
FIG. 6 is a top view of one embodiment of the flosser of the hybrid dental tool.

With reference now to FIG. 6, a top view of one embodiment of the flosser 101 is shown. As seen in FIG. 6, the bite plate 114 is located on the flossing tip 102. As depicted, the bite plate 114 includes portions having an increased width and/or thickness to facilitate the application of force to the bite plate 114 to facilitate in the penetration of the filament 108 [208??] into places between the teeth.

While various embodiments of present invention have been described, it will be apparent to those of skill in the art that many more embodiments and implementations are possible that are within the scope of this invention. Accordingly, the present invention is not to be limited to the described embodiments.

What is claimed is:

1. A hybrid dental device comprising:
    a pick comprising a shaft and a cone-shaped cleaner; and
    a flosser having a front and a back, the flosser comprising:
        a flossing portion; and
        a handle comprising:
            a pick depression on the front of the flosser, wherein the pick depression is configured to receive the shaft and the cleaner of the pick;
            a pick retainer on the front of the flosser, wherein the pick retainer is configured to retain the pick within the pick depression, wherein the pick retainer comprises:
                a channel configured to receive a portion of the pick;
                a covering extending entirely across a length of the channel; and
            wherein the handle defines a retention opening extending from the back of the flosser into the pick retainer.

2. The hybrid dental device of claim 1, wherein the flossing portion comprises a leading arm and a trailing arm connected by a link arm, wherein the link arm has a first thickness.

3. The hybrid dental device of claim 2, wherein a filament extends from the leading arm to the trailing arm.

4. The hybrid dental device of claim 2, wherein the link arm comprises a bite plate extending parallel to the filament, wherein the bite plate has a second thickness, and wherein the second thickness of the bite plate is greater than the first thickness of the link arm.

5. The hybrid dental device of claim 1, wherein the depression comprises a cleaner receptacle having a second dimension.

6. The hybrid dental device of claim 5, wherein the channel comprises a first dimension, wherein the first dimension is smaller than the second dimension, and wherein the first dimension is smaller than a width of the cleaner such that width of the cleaner prevents the cleaner from passing through the channel, wherein the width of the cleaner is measured perpendicular to the shaft of the pick.

7. The hybrid dental device of claim 6, wherein the cleaner of the pick is deformable to allow movement of the cleaner through the channel.

8. The hybrid dental device of claim 1, wherein the pick retainer comprises at least one feature configured to deformably engage with the pick.

9. The hybrid dental device of claim 1, wherein the handle comprises a connecting end and a free end, wherein the connecting end of the handle connects the handle to the flosser.

* * * * *